US010995220B2

(12) United States Patent
Anbanandam

(10) Patent No.: US 10,995,220 B2
(45) Date of Patent: May 4, 2021

(54) FUNCTIONALIZED QUATERNARY AMMONIUM HALIDES AND USE THEREOF

(71) Applicant: Agency for Science, Technology and Research, Singapore (SG)

(72) Inventor: Parthiban Anbanandam, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/558,738

(22) PCT Filed: Mar. 16, 2016

(86) PCT No.: PCT/SG2016/050120
§ 371 (c)(1),
(2) Date: Sep. 15, 2017

(87) PCT Pub. No.: WO2016/148649
PCT Pub. Date: Sep. 22, 2016

(65) Prior Publication Data
US 2018/0066145 A1    Mar. 8, 2018

(30) Foreign Application Priority Data

Mar. 16, 2015    (SG) .............................. 10201502005T

(51) Int. Cl.
*C09D 5/16*     (2006.01)
*A01N 33/12*    (2006.01)
(Continued)

(52) U.S. Cl.
CPC ........... *C09D 5/1637* (2013.01); *A01N 33/12* (2013.01); *A01N 47/12* (2013.01); *C07C 215/40* (2013.01); *C08G 18/0814* (2013.01); *C08G 18/246* (2013.01); *C08G 18/329* (2013.01); *C08G 18/3275* (2013.01); *C08G 18/758* (2013.01); *C09D 5/165* (2013.01); *C09D 175/04* (2013.01); *C09D 175/12* (2013.01); *C08G 73/02* (2013.01)

(58) Field of Classification Search
CPC ...... C07C 215/40; C09D 175/04; A01N 33/12
See application file for complete search history.

(56) References Cited

U.S. PATENT DOCUMENTS 4,128,429 A    12/1978   Wyant et al.
4,280,964 A     7/1981   Grychtol
(Continued)

FOREIGN PATENT DOCUMENTS

CN    102220080 A    10/2011
CN    103265686 A     8/2013
(Continued)

OTHER PUBLICATIONS

Suda et al. "Sequential Assembly of Phototunable Ferromagnetic Ultrathin Films with Perpendicular Magnetic Anisotropy", Angew. Chem. Int. Ed. 2009, 48, 1754-1757 (Year: 2009).*
(Continued)

*Primary Examiner* — James W Rogers
(74) *Attorney, Agent, or Firm* — Winstead PC

(57) ABSTRACT

Provision of hydroxyl group functionalized quaternary ammonium halides, photocurable or hydrolytically curable urethane based polymers thereof and their use as antifouling agents.

3 Claims, 8 Drawing Sheets

(51) Int. Cl.
*C08G 18/75* (2006.01)
*C08G 18/32* (2006.01)
*C09D 175/04* (2006.01)
*C08G 18/08* (2006.01)
*A01N 47/12* (2006.01)
*C07C 215/40* (2006.01)
*C08G 18/24* (2006.01)
*C09D 175/12* (2006.01)
*C08G 73/02* (2006.01)

(56) References Cited

U.S. PATENT DOCUMENTS

| | | | | |
|---|---|---|---|---|
| 4,411,884 | A | * | 10/1983 | Jacquet ............... A61K 8/84 424/47 |
| 4,818,797 | A | | 4/1989 | Tsuda |
| 4,891,166 | A | | 1/1990 | Schaefer et al. |
| 5,235,082 | A | | 8/1993 | Hill et al. |
| 6,008,244 | A | | 12/1999 | Willingham et al. |
| 6,479,566 | B2 | | 11/2002 | Lines et al. |
| 6,727,387 | B2 | | 4/2004 | Mukkamala et al. |
| 7,598,299 | B2 | | 10/2009 | Price |
| 8,278,400 | B2 | | 10/2012 | Chisholm et al. |
| 8,372,384 | B2 | | 2/2013 | Chisholm et al. |
| 2015/0225266 | A1 | | 8/2015 | Cho et al. |

FOREIGN PATENT DOCUMENTS

| | | |
|---|---|---|
| CN | 103304762 A | 9/2013 |
| JP | 2000103863 A | 4/2000 |
| PL | 215446 B1 | 12/2013 |
| WO | 9109915 A1 | 7/1991 |
| WO | 9951694 A1 | 10/1999 |

OTHER PUBLICATIONS

International Preliminary Report on Patentability for International Application No. PCT/SG2016/050120 dated Sep. 19, 2017, pp. 1-10.

Written Opinion of the International Searching Authority for International Application No. PCT/SG2016/050120 dated Jul. 6, 2016, pp. 1-9.

Edmond J. Gabbay, "Topography of Nucleic Acid Helices in Solutions. I.," Biochemistry, Sep. 9, 1966, vol. 5, No. 9, pp. 3036-3043, see Abstract.

Kratzer et al., "A Synthetic Route to Sulfobetaine Methacrylates with Varying Charge Distance," European Journal of Organic Chemistry, Nov. 5, 2014, vol. 2014, No. 36, pp. 8064-8071, see Abstract.

Engel et al., "Polycations. 19. The synthesis of Symmetrical Dicationic Lipids with Internal Dimethylazonia Functionalities Separated by a Spacer Unit and Pendant Chains," Chemistry and Physics of Lipds, vol. 160, No. 2, May 3, 2009, pp. 105-108, see Abstract.

Edmond J. Gabbay, "Topography of Nucleic Acid Helices in Solutions. I.," Biochemistry, Sep. 9, 1966, vol. 5, No. 9, pp. 3036-3043.

Kratzer et al., "A Synthetic Route to Sulfobetaine Methacrylates with Varying Charge Distance," European Journal of Organic Chemistry, Nov. 5, 2014, vol. 2014, No. 36, pp. 8064-8071.

Engel et al., "Polycations. 19. The synthesis of Symmetrical Dicationic Lipids with Internal Dimethylazonia Functionalities Separated by a Spacer Unit and Pendant Chains," Chemistry and Physics of Lipds, vol. 160, No. 2, May 3, 2009, pp. 105-108.

Kim et al., "Antifouling Paint Resin Based on Polyurethane Matrix with Quaternary Ammonium Salt," Polymer (Korea), vol. 39, No. 1, Jan. 31, 2015, pp. 122-129, see Abstract, full text available only online at http://www.koreascience.or.kr/article/JAK0201506849872151.pdf.

Hazziza-Laskar et al., "Biocidal Polymers Active by Contact. I. Synthesis of Polybutadiene with Pendant Duatemary Ammonium Groups," Journal of Applied Polymer Science, vol. 50, 1993, pp. 651-662.

Nurdin et al., "Biocidal Polymers Active by Contact. II. Biological Evaluation of Polyurethane Coatings with Pendant Quaternary Ammonium Salts," Journal of Applied Polymer Science, vol. 50, 1993, pp. 663-670.

Hazziza-Laskar et al., "Biocidal Polymers Active by Contact. IV. Polyurethanes Based on Polysiloxanes with Pendant Primary Alcohols and Quaternary Ammonium Groups," Journal of Applied Polymer Science, vol. 58, 1995, pp. 77-84.

Sauvet et al., "Biocidal Polymers Active by Contact. V. Synthesis of Polysiloxanes with Biocidal Activity," Journal of Applied Polymer Science, vol. 75, 2000, pp. 1005-1012.

Tatsuo Tashiro, "Antibacterial and Bacterium Adsorbing Macromolecules," Macromolecular Materials and Engineering, vol. 286, 2001, pp. 63-87.

Gottenbos et al., "In Vitro and in Vivo Antimicrobial Activity of Covalently Coupled Quaternary Ammonium Silane coatings on Silicone Rubber," Biomaterials, vol. 23, 2002, pp. 1417-1423.

Klun et al., "Structure-Property Relationships of Ionene Polymers," Journal of Polymer Science: Part A: Polymer chemistry, vol. 25, 1987, pp. 87-109.

* cited by examiner 5 weeks  6 weeks

Uncoated

Primer coated       Polymer 5 with primer

US 10,995,220 B2

FUNCTIONALIZED QUATERNARY AMMONIUM HALIDES AND USE THEREOF

CROSS-REFERENCE TO RELATED APPLICATION

This application claims the benefit of priority of Singapore Patent Application No. 10201502005T, filed 16 Mar. 2015, the contents of which being hereby incorporated by reference in its entirety for all purposes.

TECHNICAL FIELD

Various embodiments relate generally to the preparation of functional quaternary ammonium salts. More particularly, various embodiments relate to the preparation of hydroxyl group functionalized quaternary ammonium halides. Various embodiments also relate to the preparation of photocurable quaternary ammonium halides from the hydroxyl group functionalized quaternary ammonium halides. In other embodiments, preparation of hydrolytically curable quaternary ammonium halide derivatives by a sol-gel process is also disclosed. Said hydroxyl group functionalized quaternary ammonium halides are useful for making polymers, which are useful as water insoluble, non-leaching, active by contact antifouling materials.

BACKGROUND

Quaternary ammonium salts have many applications such as ion exchange resins, phase transfer catalysts, structure directing agents in the preparation of zeolites, components of cosmetics & personal care formulations, photovoltaic cells, flocculating agents for water purification applications, antimicrobial agents, antistatic agents, etc. Earliest reports on quaternary ammonium salt bearing polymers, which are sometimes referred to as polyionenes, date back to early 1930s. Quaternary ammonium salts are well known cationic disinfectants and their bactericidal properties are known for many decades. Quaternary ammonium salts which are attached to polymers and are thus made water insoluble biocides have many advantages. These water insoluble biocides are non-leaching in nature and thus their activity is retained for longer periods of time than biocides that function by leaching. Since leaching causes environmental concerns due to the fact that it releases toxic compounds, biocides which possess biocidal activity by contact are therefore more preferred.

One of the problems facing man-made structures immersed in water is the unwanted settlement and growth of water borne organisms. This process, which is referred to as biofouling, is caused by both micro- and macro-organisms. Biofouling leads to many problems ranging from poor performance of materials, shortened durability, increased weight and drag on water bound moving vehicles such as ships which cause higher fuel consumption as well as transport of marine organisms from one geographical location to another, a phenomenon called species invasion. Until recently, the problem of biofouling was tackled by the use of heavy metal leaching coatings which have caused environmental problems. As an alternative to this, quaternary ammonium salt bearing compounds have been proposed as suitable environmentally friendly alternatives.

U.S. Pat. Nos. 4,891,166 and 5,235,082 disclose polysiloxane ionomers with quaternary ammonium salt groups. These quaternary ammonium chloride units improve the compatibility of polysiloxanes with organic polymers and introduce antimicrobial and anti-electrostatic properties to the materials to make them applicable for fabric conditioning agents, bactericides, textile finishing and plastic processing. U.S. Pat. No. 4,818,797 disclose ammonium carboxylates. WO 9951694 discloses denatonium capsaicinate and WO 9109915 disclose quaternary ammonium salts derived from sulfonic acids. U.S. Pat. No. 6,727,387 disclose quaternary ammonium salts having tertiary alkyl groups. U.S. Pat. No. 6,479,566 discloses the preparation of acid groups blocked by quaternary ammonium groups. U.S. Pat. No. 7,598,299 disclose quaternary ammonium salts formed with palmitate. U.S. Pat. No. 4,128,429 disclose quaternary ammonium salts of benzyl bromide and tertiary amines containing tributyl stannyl ether moiety. U.S. Pat. No. 6,008,244 discloses a halopropargyl ammonium compound. U.S. Pat. Nos. 8,278,400 and 8,372,384 disclose quaternary ammonium salt functionalized crosslinked polyalkylsiloxanes.

Quaternary ammonium salts have been grafted onto polyvinyl chloride and coatings prepared from such polymers exhibited better biocidal properties than classical paints containing organo tin compounds during two months in sea water. However, the efficiency decreased after this period (J. Hazziza-Laskar et al., *J. Appl. Polym. Sci.* (1993) 50, 651-662). Bioactivity of quaternary ammonium salts was determined by contact and diffusion processes (N. Nurdin et al. *J. Appl. Polym. Sci.* (1993) 50, 663-670). Bioactivity was measured in linear alkyl bromides from $C_8$ to $C_{16}$ carbon atoms. After 1 h, the bioactivity measured was practically independent of the length of the alkyl chain. For chains with 12, 14 and 16 carbon atoms the coatings exhibited no diffusion thereby confirming activity by contact whereas for 8 and 10 carbon atoms a zone of inhibition was observed. The location of the quaternary ammonium salt at the free extremity of a flexible side chain is a very important factor. Polymers bearing pendant quaternary ammonium salts are useful for formulating new biocidal coatings that have the advantage of being non-polluting. More importantly, the activity may be permanent because the biocidal group is not consumed during the course of interaction with microorganisms. This is contrary to leaching where loss of activity with time is accompanied with environmental problems caused by the high toxicity of the released compounds. Thus, these quaternary ammonium salt containing polymers are a class of biocidal polymers for a variety of microorganisms only by contact in the absence of diffusion of any toxic substance.

In the case of polymeric quaternary ammonium salts, the polymers are far more active than the corresponding monomers. Poly(trialkylvinylbenzyl ammonium chloride) and poly(N-benzyl-4-vinylpyridinium bromide) were found to be more active than the corresponding monomers (J. Hazziza-Laskar et al. *J. Appl. Polym. Sci.* (1995) 58, 77-84). The higher activity of the quaternary ammonium salt bearing polymers is due to larger density of charges on the polymer making their interaction with cellular wall of microorganisms more efficient (G. Sauvet et al. *J. Appl. Polym. Sci.* (2000) 75, 1005-1012). It has been reported that crosslinked polyvinyl pyridinium halide captured bacterial cells by electrostatic interaction but allowed the microorganisms to live.

A reactive silane developed by Dow Corning, DC 5700, $(MeO)_3Si(CH_2)_3N^+Me_2C_{18}H_{37}Cl$ reacted with many surfaces such as glass, cotton, polyester fibers or polyurethane foams. The materials treated with DC 5700 showed algicidal and bactericidal properties that are maintained after repeated washings and no apparent leaching was observed. However, a vulcanized silicon elastomer obtained by reacting DC 5700 with polydimethylsiloxane (PDMS) terminated with —OH groups, exhibited leaching and its biocidal activity was lost upon subjecting the elastomer to Soxhlet extraction.

There is a demand for insoluble antibacterial macromolecules. Such polymers could be utilized as sterilizers and packaging materials in drinking water and food applications (T. Tashiro, *Macromol. Mater. Eng.* (2001), 286, 63-87). Quaternary ammonium salt derived disinfectants have been proposed to be suitable for preventing biomaterial centered infections. The biomaterials are functionalized with quaternary ammonium salts and since no antimicrobial agent is leached, long term protection against bacterial colonization can be ensured. The antimicrobial effects of soluble quaternary ammonium compounds increase with the length of alkyl moieties on the N atom with the optimum chain length of 16-18 carbon atoms (B. Gottenbos et al. *Biomaterials*, (2002), 23, 1417-1423).

All of the quaternary ammonium salts described above are non-functional in the sense that they do not carry additional functional groups like hydroxyl (OH) which would be useful for making various polymers such as polyethers, polyesters, or polyurethanes. Such modification would help to render the quaternary ammonium salt bearing polymers insoluble in aqueous media, thereby avoiding issues such as leaching. Hence, polymers of this nature are perfect candidates for making surfaces active by contact. Thus, when one attempts to synthesize such functionalized quaternary ammonium salts, some of the factors to consider include: ease of producing such functionalized quaternary ammonium salts, ease of availability of starting materials in bulk quantities, toxicity of the reagents, stability of the starting materials, preserving the surface activity by contact for prolonged periods, wide spectrum of activity, etc.

There have been two reports on the preparation of hydroxyl group functionalized quaternary ammonium salts. J. Hazziza-Laskar et al., (*J. Appl. Polym. Sci.* (1993) 50, 651-662) reported the hydroxyl group functionalized quaternary ammonium salts bearing siloxane pendant groups. Quaternary ammonium salts were introduced as lateral substituents by chemical modification of a macromolecular polyol such as hydroxy telechelic polybutadiene. This reaction suffers from many disadvantages such as isomerization, excess use of costly reagents, unreliable number of terminal functional groups, difficulties in purification of polymers, presence of unwanted synthetic residues in the polymers which leached upon immersing in water, thereby compromising the concept of surface activity by contact, difficulty to remove unreacted bromide used for quaternization, isocyanates remaining in excess due to uncertain hydroxyl functionalities because of which the films swelled rapidly and broke up in water, low concentration of quaternary ammonium groups, etc.

Thomas P. Klun et al. (*J. Polym. Sci.: Part A: Polym. Chem.* (1987)) reported the preparation of tertiary amino secondary alcohols by the ring opening of epoxides using carboxylic acids in the presence of toxic metal salts like chromium (III) salts. There are many problems associated with this process, such as reversible reaction, elimination, thermal instability of quaternary ammonium salts, slow reaction, poor conversion, etc. More importantly, the tertiary amines obtained were moderately high in molecular weight, in the range of above 1,000 to about 6,000. Because of this high molecular weight nature of starting material undergoing quaternization, quaternary ammonium salt formed remained inherently diluted, effectively reducing its antimicrobial activity. Such quaternary ammonium salts are purposely built to be useful as antistatic agents rather than disinfectants.

From the foregoing discussion, it is therefore clear that there remains a need to provide for functional quaternary ammonium salts and their corresponding polymers which can be prepared in a much simpler and high yield process, preferably from readily available starting materials by a one-step process. It is even more desirable to prepare multiple functional quaternary ammonium salts bearing more than one quaternary ammonium group.

SUMMARY

It is herein described the development of specialty polymers which protect surfaces immersed in sea against the settlement of marine organisms. Specifically, dihydroxy functionalized quaternary ammonium salts were designed, synthesized and polymerized. These polymers were found to exhibit very good antifouling characteristics. The developed polymers completely prevented the settlement of tubeworms (one of the dominant fouling organisms in Singapore) over six weeks. The sample slides immersed in sea were also free of growth of algae.

Advantageously, the application of the dihydroxy functionalized quaternary ammonium salts bearing polymers is free of heavy metals and is a non-release based approach. Further, the polymers render surfaces active by contact mechanism and activity can be established after mixing with a commercial primer used in marine applications. The developed process has been further extended to photocuring and sol gel processes.

Thus, according to various embodiments, there is provided a quaternary ammonium halide of Formula (I)

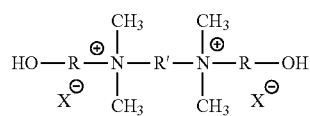

wherein:

X is Br or Cl;

R is selected from the group consisting of $C_1$-$C_{20}$ alkyl, $C_6$-$C_{14}$ aryl, $C_3$-$C_8$ heteroaryl, $C_3$-$C_{20}$ cycloalkyl, and $C_7$-$C_{20}$ aralkyl;

R' is selected from the group consisting of $C_1$-$C_{20}$ alkyl, $C_3$-$C_{20}$ cycloalkyl, $C_7$-$C_{20}$ aralkyl, and $C_2$-$C_{15}$ alkenyl.

According to various embodiments, there is provided a polymer comprising:

(A) a quaternary ammonium halide of Formula (I) linked through urethane linkage; or (B)

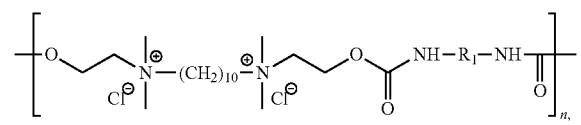

wherein $R_1$ is $C_6$-$C_{20}$ alkylcycloalkyl, preferably

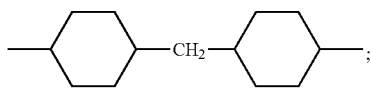

n is any integer from 1 to 100; or
(C)

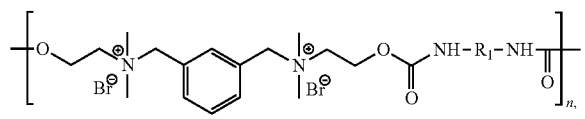

wherein $R_1$ is $C_6$-$C_{20}$ alkylcycloalkyl, preferably

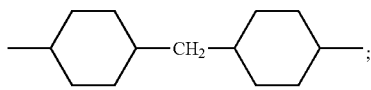

n is any integer from 1 to 100; or
(D) a first quaternary ammonium halide of Formula (I) coupled to a second quaternary ammonium halide of Formula (I) via a urethane linkage, wherein the first quaternary ammonium halide of Formula (I) is the same as or different from the second quaternary ammonium halide of Formula (I); or
(E) a quaternary ammonium halide of Formula (I) coupled to a quaternary ammonium halide of Formula (II) via a urethane linkage,

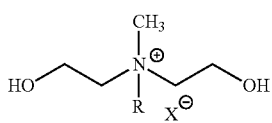

wherein:
X is Br or Cl;
R is selected from the group consisting of $C_1$-$C_{20}$ alkyl, $C_3$-$C_{20}$ cycloalkyl, $C_7$-$C_{20}$ aralkyl, and $C_2$-$C_{15}$ alkenyl.

According to various embodiments, there is provided a method of making a surface antifouling, comprising coating the surface with a polymer disclosed herein.

According to various embodiments, there is provided a method for making a quaternary ammonium halide of Formula (I), comprising reacting a tertiary amino primary alcohol with a dihaloaliphatic compound or a dihaloaralkyl compound.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

Figure 1:
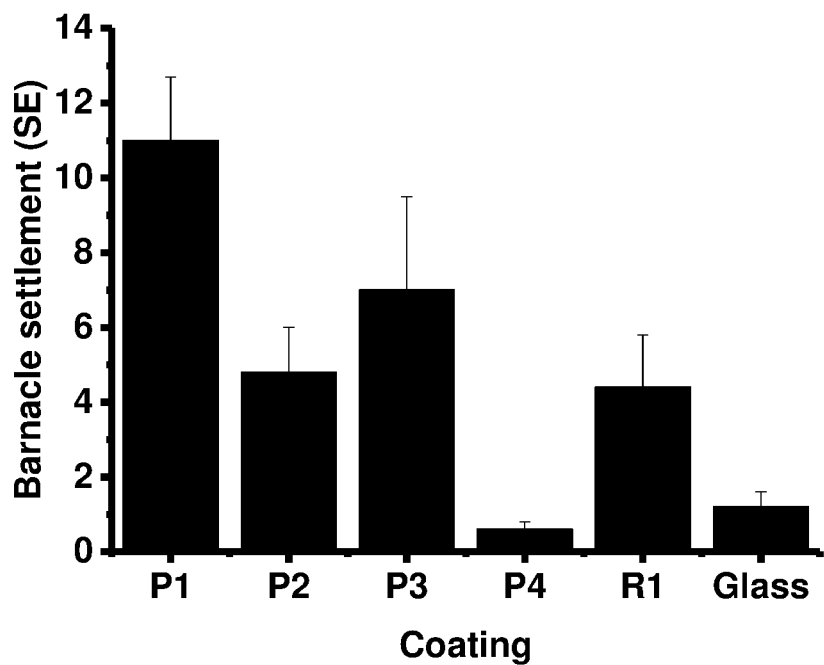
FIG. 1 is a chart that shows settlement of barnacles on polyurethanes derived from diols bearing mono quaternary ammonium salt (after 2 weeks) (R1—glass coated with primer; Glass—uncoated glass).

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

According to various embodiments, there is disclosed a quaternary ammonium halide of Formula (I)

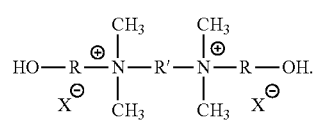

Formula (I) comprises two quaternary ammonium cations. In other words, the compound of Formula (I) is a diquaternary ammonium halide. For brevity and convenience sake, a quaternary ammonium halide is simply referred to in the present disclosure.

In Formula (I), X, at each occurrence, is a halide, such as F, Br or Cl. In other words, both X can be the same or different. In one embodiment, one X can be Br while the other X can be Cl. In another embodiment, both X can be Br. In yet another embodiment, both X can be Cl. Other combinations of suitable halides are also possible.

In various preferred embodiments, both X are Br or Cl.

In Formula (I), R, at each occurrence, is selected from the group consisting of $C_1$-$C_{20}$ alkyl, $C_6$-$C_{14}$ aryl, $C_3$-$C_8$ heteroaryl, $C_3$-$C_{20}$ cycloalkyl, and $C_7$-$C_{20}$ aralkyl. In other words, both R can be the same or different.

In Formula (I), R' is selected from the group consisting of $C_1$-$C_{20}$ alkyl, $C_3$-$C_{20}$ cycloalkyl, $C_7$-$C_{20}$ aralkyl, and $C_2$-$C_{15}$ alkenyl.

The term "aliphatic", alone or in combination, refers to a straight chain or branched chain hydrocarbon comprising at least one carbon atom. Aliphatics include alkyls, alkenyls, and alkynyls. In certain embodiments, aliphatics are optionally substituted, i.e. substituted or unsubstituted. Aliphatics include, but are not limited to, methyl, ethyl, propyl, isopropyl, butyl, isobutyl, tert-butyl, pentyl, hexyl, ethenyl, propenyl, butenyl, ethynyl, butynyl, propynyl, and the like, each of which may be optionally substituted. As used herein, aliphatic is not intended to include cyclic groups.

The term "alkyl", alone or in combination, refers to a fully saturated aliphatic hydrocarbon. In certain embodiments, alkyls are optionally substituted. In certain embodiments, an alkyl comprises 1 to 20 carbon atoms, for example 1 to 10 carbon atoms, wherein (whenever it appears herein in any of the definitions given below) a numerical range, such as "1 to 20" or "$C_1$-$C_{20}$", refers to each integer in the given range, e.g. "$C_1$-$C_{20}$ alkyl" means an alkyl group comprising 1 carbon atom, 2, 3, 4, 5, 6, 7, 8, 9, 10, 11, 12, 13, 14, 15, 16, 17, 18, 19 or 20 carbon atoms. Examples of alkyl groups include, but are not limited to, methyl, ethyl, n-propyl, isopropyl, n-butyl, isobutyl, sec-butyl, tert-butyl, tert-amyl, pentyl, hexyl, heptyl, octyl and the like.

The term "alkenyl", alone or in combination, refers to an aliphatic hydrocarbon having one or more carbon-carbon double-bonds, such as two or three carbon-carbon double-bonds. In certain embodiments, alkenyls are optionally substituted, i.e. substituted or unsubstituted. In certain embodiments, an alkenyl comprises 2 to 15 carbon atoms. "$C_2$-$C_{15}$ alkenyl" means an alkenyl group comprising 2, 3, 4, 5, 6, 7, 8, 9, 10, 11, 12, 13, 14, or 15 carbon atoms. Examples of alkenyls include, but are not limited to, ethenyl, propenyl, butenyl, 1,4-butadienyl, pentenyl, hexenyl, 4-methylhex-1-enyl, 4-ethyl-2-methylhex-1-enyl and the like.

The term "cyclo", "cyclic" or "carbocycle" refers to a group comprising a covalently closed ring, wherein each of the atoms forming the ring is a carbon atom. A cyclic ring may be formed by 3, 4, 5, 6, 7, 8, 9, 10, 11, 12, 13, 14, 15, 16, 17, 18, 19 or 20 carbon atoms. Carbocycles may be optionally substituted. Accordingly, a $C_3$-$C_{20}$ cycloalkyl is a $C_3$-$C_{20}$ alkyl except that the alkyl group is not aliphatic but cyclic. Examples of cycloalkyl groups include, but are not limited to, cyclopropane, cyclobutane, cyclopentane, cyclohexane and the like.

The term "aromatic" refers to a group comprising a covalently closed planar ring having a delocalized π-electron system comprising 4n+2 π electrons, where n is an integer. Aromatic rings may be formed by 5, 6, 7, 8, 9 or more atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_1$-$C_6$ alkoxy, a $C_1$-$C_6$ alkyl, a $C_1$-$C_6$ hydroxyalkyl, a $C_1$-$C_6$ aminoalkyl, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic ring wherein each of the atoms forming the ring is a carbon atom. Aryl rings may be formed by 5, 6, 7, 8, 9 or more carbon atoms. Aryl groups may be optionally substituted. In certain embodiments, aryls are optionally substituted, i.e. substituted or unsubstituted. In certain embodiments, an aryl comprises 6 to 14 carbon atoms. "$C_6$-$C_{14}$ aryl" means an aryl group comprising 6, 7, 8, 9, 10, 11, 12, 13, or 14 carbon atoms. Accordingly, "$C_7$-$C_{20}$ aralkyl" means an aryl group bound to an alkyl group. Examples of aralkyls include, but are not limited to, 3-methylphenyl, 4-methylphenyl, dimethylphenyl and the like.

The term "heteroaryl" refers to an aromatic heterocycle. Heteroaryl rings may be formed by four, five, six, seven, eight, nine, or more than nine atoms. Heteroaryls may be optionally substituted. Examples of heteroaryl groups include, but are not limited to, aromatic $C_3$-$C_8$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_1$-$C_6$-alkoxy, $C_1$-$C_6$-alkyl, $C_1$-$C_6$-hydroxyalkyl, $C_1$-$C_6$-aminoallcyl, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline.

The term "optionally substituted" or "substituted or unsubstituted" refers to a group in which none, one, or more than one of the hydrogen atoms have been replaced with one or more groups such as, but are not limited to, alkyl, heteroalkyl, haloalkyl, heterohaloalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups. In embodiments in which two or more hydrogen atoms have been substituted, the substituent groups may be linked to form a ring.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

According to various preferred embodiments, in Formula (I) R' comprises a $C_1$-$C_{20}$ alkyl, and more preferably a $C_1$-$C_{10}$ alkyl.

In certain preferred embodiments, in Formula (I) R' is —(CH$_2$)$_4$— or —(CH$_2$)$_{10}$—.

In alternative various preferred embodiments, in Formula (I) R' comprises a C$_7$-C$_{20}$ aralkyl, and more preferably a C$_7$-C$_{10}$ aralkyl.

In certain various preferred embodiments, in Formula (I) R' is

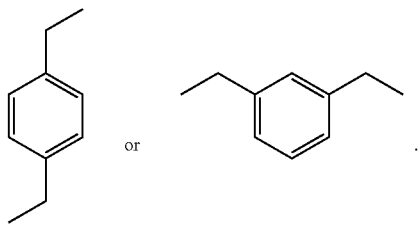

In various preferred embodiments, in Formula (I) R, at each occurrence, comprises a C$_1$-C$_{20}$ alkyl, and more preferably a C$_1$-C$_{10}$ alkyl.

According to one preferred embodiment, in Formula (I) R, at each occurrence, is —(CH$_2$)$_2$—.

A method for making the quaternary ammonium halide of Formula (I) according to various embodiments is next described. The method comprises reacting a tertiary amino primary alcohol with a dihaloaliphatic compound or a dihaloaralkyl compound.

In one embodiment, the tertiary amino primary alcohol may be

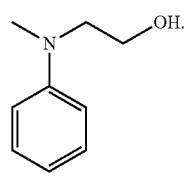

In various embodiments, the dihaloaliphatic compound may be 1,2-dichloroethane, 1,3-dichloropropane, 1,4-dichlorobutane, 1,5-dichloropentane, 1,6-dichlorohexane, 1,7-dichloroheptane, 1,8-dichlorooctane, 1,9-dichlorononane, 1,10-dichlorodecane, 1,2-dibromoethane, 1,3-dibromopropane, 1,4-dibromobutane, 1,5-dibromopentane, 1,6-dibromohexane, 1,7-dibromoheptane, 1,8-dibromooctane, 1,9-dibromononane, 1,10-dibromodecane.

In various embodiments, the dihaloaralkyl compound may be

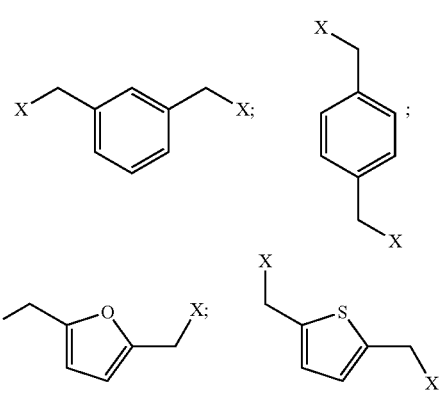

X = Cl or Br or a regioisomer thereof.

According to various embodiments, the tertiary amino primary alcohol comprises N—N-dimethylaminoethanol.

According to various embodiments, the dihaloaliphatic compound comprises 1,10-dichlorodecane.

According to various embodiments, the dihaloaralkyl compound comprises α,α'-dibromo-m-xylene.

As mentioned in earlier paragraphs, the disclosed quaternary ammonium halides of Formula (I) is rendered functional (e.g. in terms of solubility in aqueous media) by virtue of the two terminal hydroxyl (—OH) groups. The inventor has surprisingly found that such functional quaternary ammonium halides can be extended to form polymers and for using in other techniques such as UV curing and sol-gel processes. The quaternary ammonium halides of Formula (I) and their corresponding polymers find particular use in preventing settlement of micro- and macro-organisms on a surface. Advantageously, the quaternary ammonium halides of Formula (I) and their corresponding polymers are free of heavy metals and the mechanism of antifouling action is not based on leaching.

Thus, according to various embodiments, there is provided a polymer comprising:

(A) a quaternary ammonium halide of Formula (I) linked through urethane linkage; or (B)

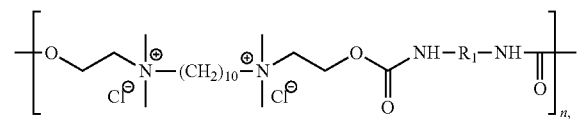

wherein R$_1$ is C$_6$-C$_{20}$ alkylcycloalkyl, preferably

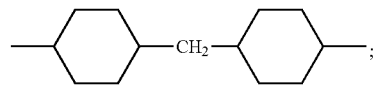

n is any integer from 1 to 100; or (C)

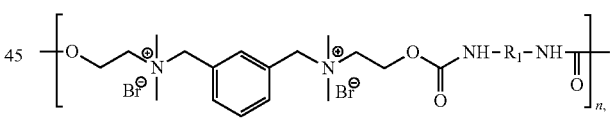

wherein R$_1$ is C$_6$-C$_{20}$ alkylcycloalkyl, preferably

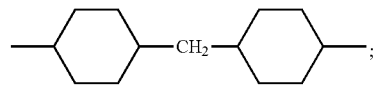

n is any integer from 1 to 100; or (D) a first quaternary ammonium halide of Formula (I) coupled to a second quaternary ammonium halide of Formula (I) via a urethane linkage, wherein the first quaternary ammonium halide of Formula (I) is the same as or different from the second quaternary ammonium halide of Formula (I); or (E) a quaternary ammonium halide of Formula (I) coupled to a quaternary ammonium halide of Formula (II) via a urethane linkage, II
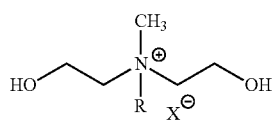
wherein:
X is Br or Cl;
R is selected from the group consisting of $C_1$-$C_{20}$ alkyl, $C_3$-$C_{20}$ cycloalkyl, $C_7$-$C_{20}$ aralkyl, and $C_2$-$C_{15}$ alkenyl.
In various embodiments, n may be any integer from 10 to 50.
In various preferred embodiments, the polymer is:
P5
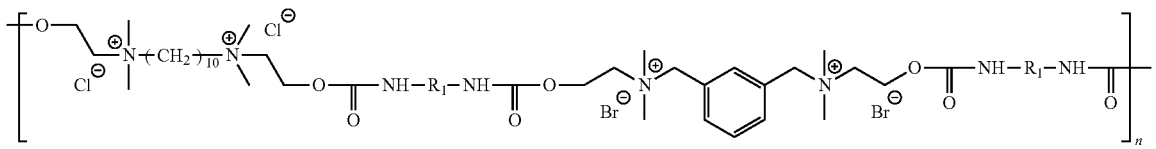
wherein $R_1$ is $C_6$-$C_{20}$ alkylcycloalkyl, preferably
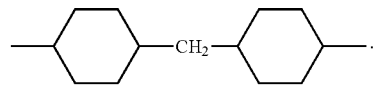
In yet other various preferred embodiments, the polymer is one of:
P6
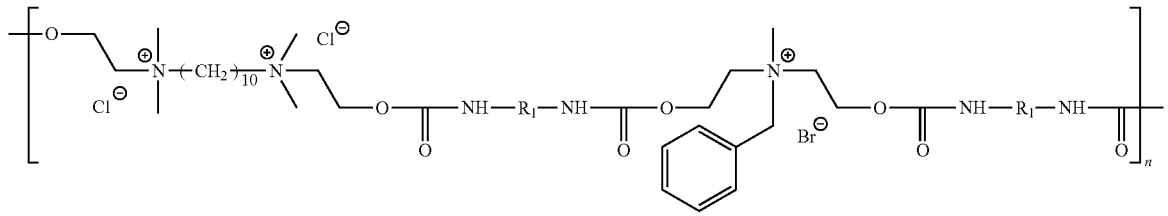
P7
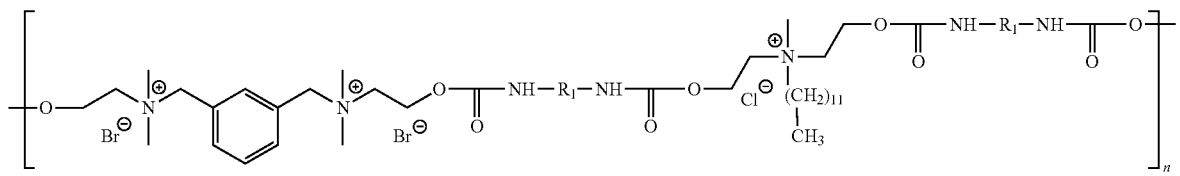
P8
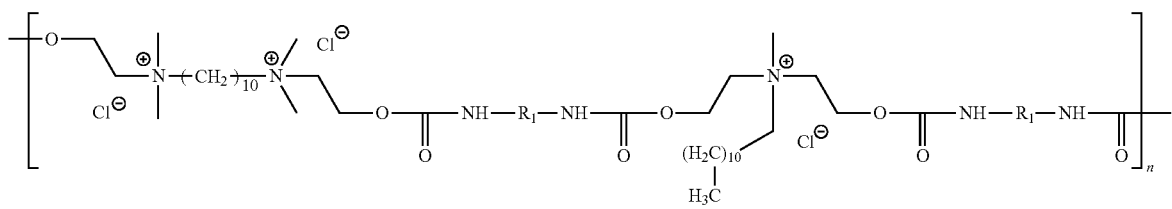

wherein $R_1$ is $C_6$-$C_{20}$ alkylcycloalkyl, preferably

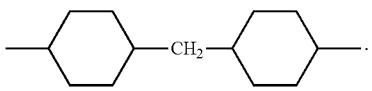

As mentioned earlier, a surface may be made antifouling by coating the surface with a polymer disclosed herein (i.e. an active by contact surface is obtained). Various coating techniques may be used to coat or deposit a layer of the polymer onto the surface. In one example, the polymer may be coated with the use of doctor blade. Another technique of coating includes spin coating a solution of the polymer onto the surface and allowing the polymer to develop.

In cases where the surface to be protected forms part of a marine vessel, for example, it is preferred that prior to coating the surface, the polymer is first blended with a primer used in marine coatings. An example of a commercial primer used in marine coatings may be Primacon.

The presently disclosed quaternary ammonium halide bearing polymers may also find use in photocuring processes. As an example, the polymers (or oligomers) terminated with hydroxyl groups can be used to link with isocyanate bearing methacrylates and simultaneously cured by UV light or modified to terminate with (meth)acrylates and cured with other vinyl monomers by UV light.

A further use of the presently disclosed quaternary ammonium salt bearing polymers may lie in sol-gel processes. As an example, the polymers (or its oligomers) terminated with hydroxyl groups can be condensed with tetraalkoxy silanes (or derivatives thereof), tetraacetoxy silanes (or derivatives thereof), or isocyanate bearing triethoxy silanes in a sol-gel process.

In order that the invention may be readily understood and put into practical effect, particular embodiments will now be described by way of the following non-limiting examples.

EXAMPLES

Preparation of Functional Quaternary Ammonium Salts and Antifouling Evaluation in the Sea An attempt was made to find out the efficacy of various structural motifs, namely, four alkyl and aralkyl halides were chosen to make quaternary ammonium salts viz. benzyl bromide, benzyl chloride, dodecyl bromide and dodecyl chloride.

Hydroxyl group functionalized diol monomers were prepared from these alkyl and aralkyl halides as shown in Scheme 1.

Scheme 1. Preparation of diol monomers bearing one quaternary ammonium salt

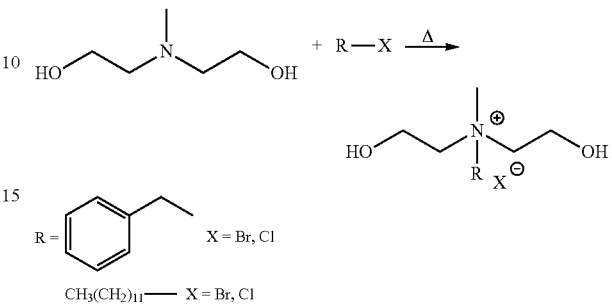

Polyurethanes were prepared from the quaternary ammonium salt bearing diols as shown in Scheme 2.

Scheme 2. Preparation of homo polyurethanes from diol monomers bearing one quaternary ammonium salt

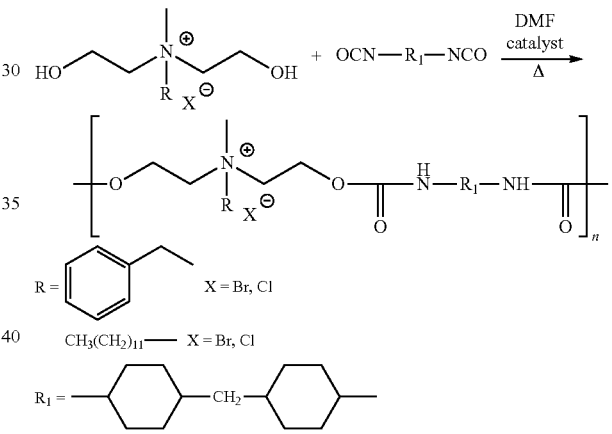

In addition to these homo polyurethanes, some copolyurethanes were also prepared and evaluated. The preparation of copolyurethanes is shown in Scheme 3.

Scheme 3. Preparation of copolyurethanes from diol monomers bearing one quaternary ammonium salt

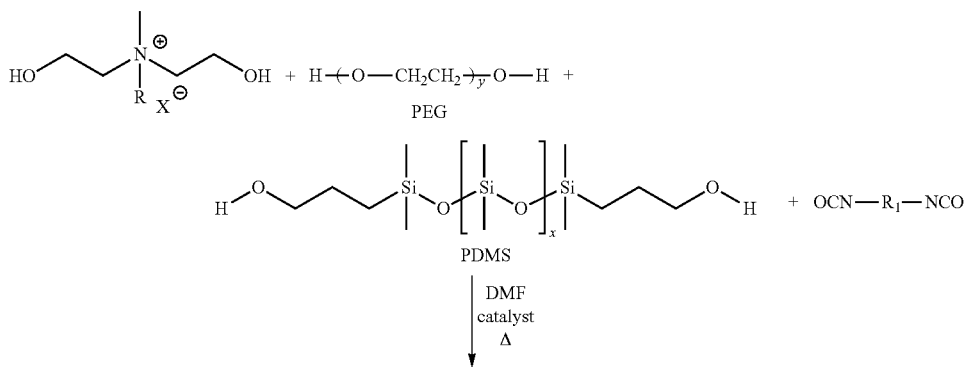

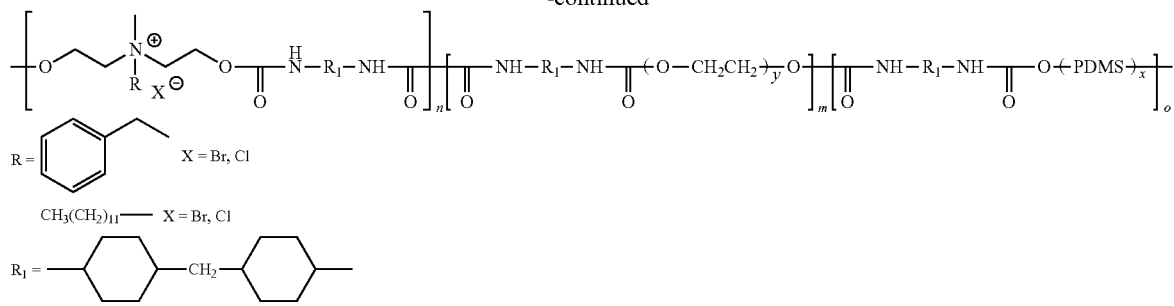

Figure 2:
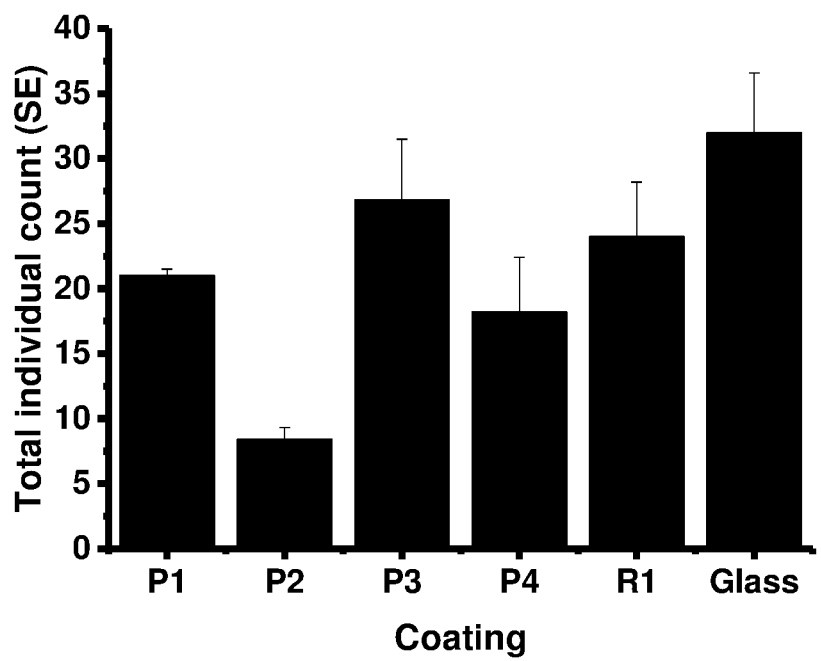
FIG. 2 is a chart that shows settlement of tubeworms on polyurethanes derived from diols bearing mono quaternary ammonium salt (after 2 weeks).
Figure 3:
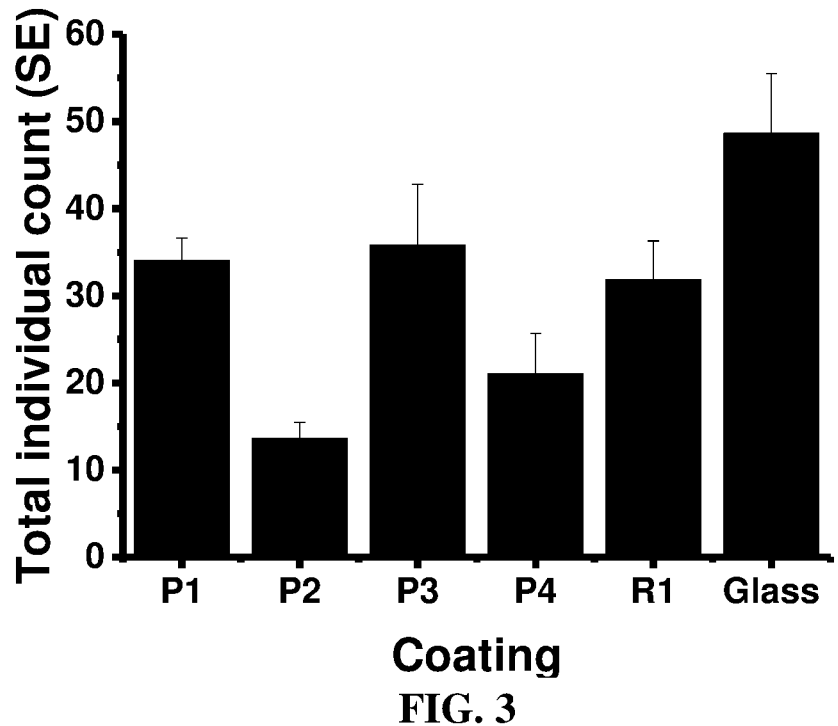
FIG. 3 is a chart that shows antifouling behavior of polyurethanes derived from diols bearing mono quaternary ammonium salt (after 2 weeks).

These polyurethanes were dissolved in methanol to make 50 wt % polymer solution. The polymer solution was then mixed with a commercial antifouling primer like Primacon and coated on frosted glass slides (7 cm long, 2.5 cm wide). Each polymer solution mixed with primer was coated with the help of an applicator on five such glass slides placed parallel to each other and allowed to dry under ambient conditions in a fume hood. After drying for a week, the glass slides were subjected to leachate test, followed by immersion in sea. Among the quaternary ammonium salt bearing polyurethanes, those copolyurethanes derived from benzyl bromide and dodcecyl chloride showed some antifouling activity as compared to the blank glass slide and the slide coated with primer alone as shown in FIGS. 1, 2 and 3. However, the antifouling activity observed after two weeks of exposure in sea was far from desirable. It is also interesting to note that they acted in a unique way, e.g. copolyurethanes bearing quaternary ammonium salt derived from dodecyl chloride was active against barnacles and that of benzyl bromide was active against tubeworms. In general, the copolyurethanes showed better antifouling activity than the homo polyurethanes.

Figure 4:
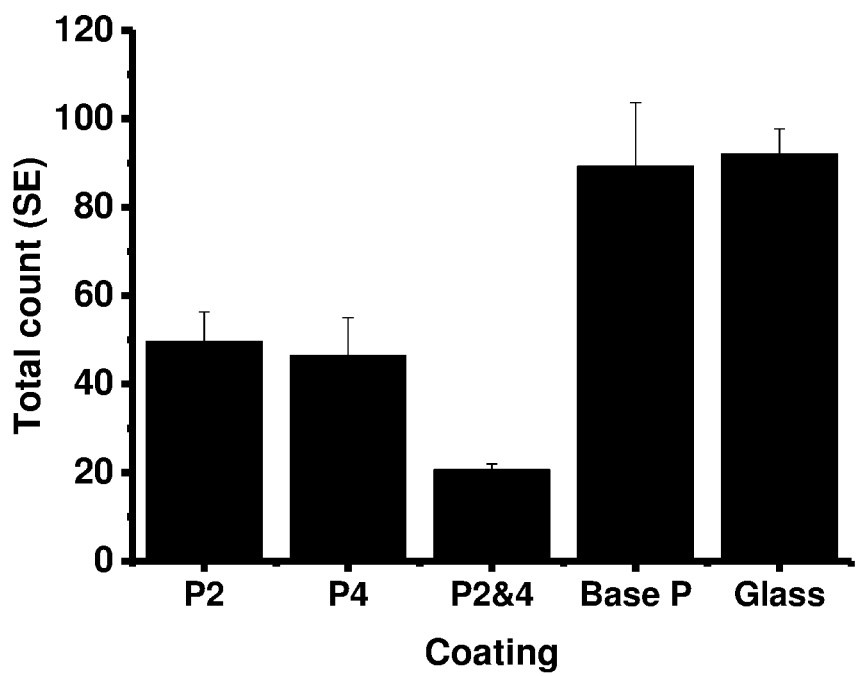
FIG. 4 is a chart that shows antifouling behavior of physical blends polyurethanes derived from diols bearing mono quaternary ammonium salts (after 4 weeks) (Base P—glass coated with film forming polymer; Glass—uncoated glass slide).

In order to see the effect of physical blend of homo polyurethanes derived from dodecyl chloride and benzyl bromide, a 1:1 mixture of these polymers were dissolved in methanol. The methanol solution was then mixed with a film forming polymer and coated on a glass slide. The glass slide was then evaluated in the same manner as that of primer blended polyurethanes. After 4 weeks of exposure in sea water, the physical blend exhibited superior antifouling performance as compared to that of the respective homo polyurethanes as well as blank and base polymer as shown in FIG. 4. However, still the antifouling performance is well below the desired level.

Figure 5:
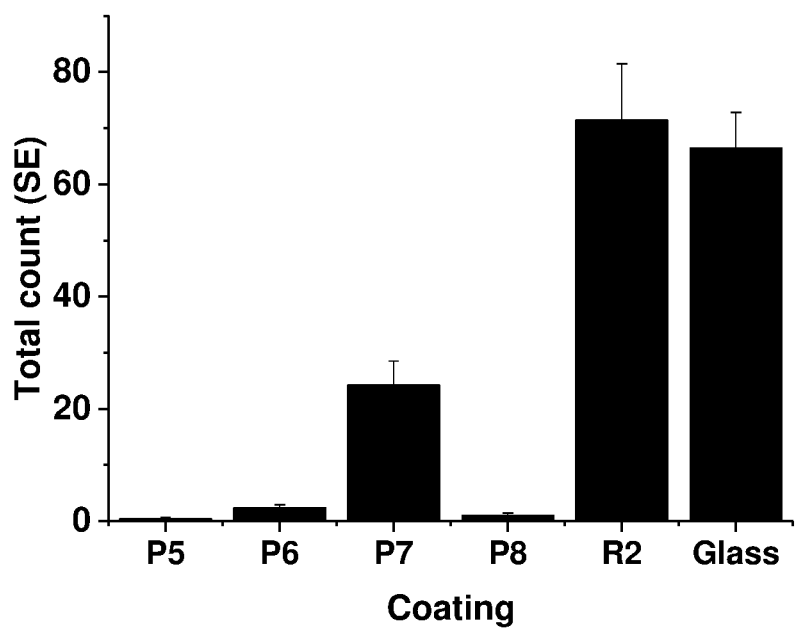
FIG. 5 is a chart that shows antifouling performance of polyurethanes derived from diols bearing two quaternary ammonium salts (after 2 weeks) (R2—glass coated with primer; Glass—uncoated glass slide).
Figure 6:
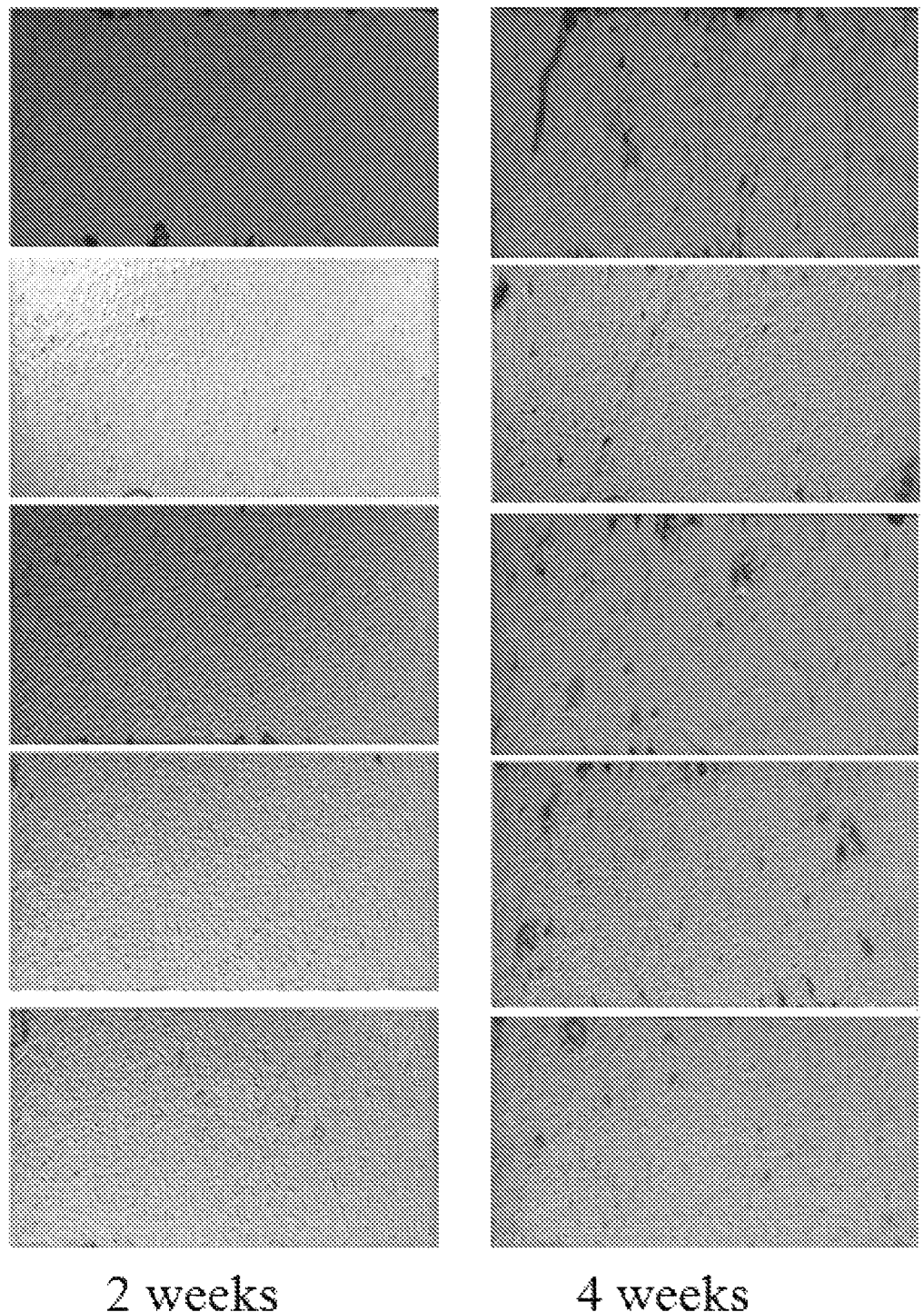
FIG. 6 is a photograph that shows the appearance of coated glass slides after various periods of immersion. The glass slides are coated with selected polyurethanes derived from diols bearing two quaternary ammonium salts.
Figure 6:
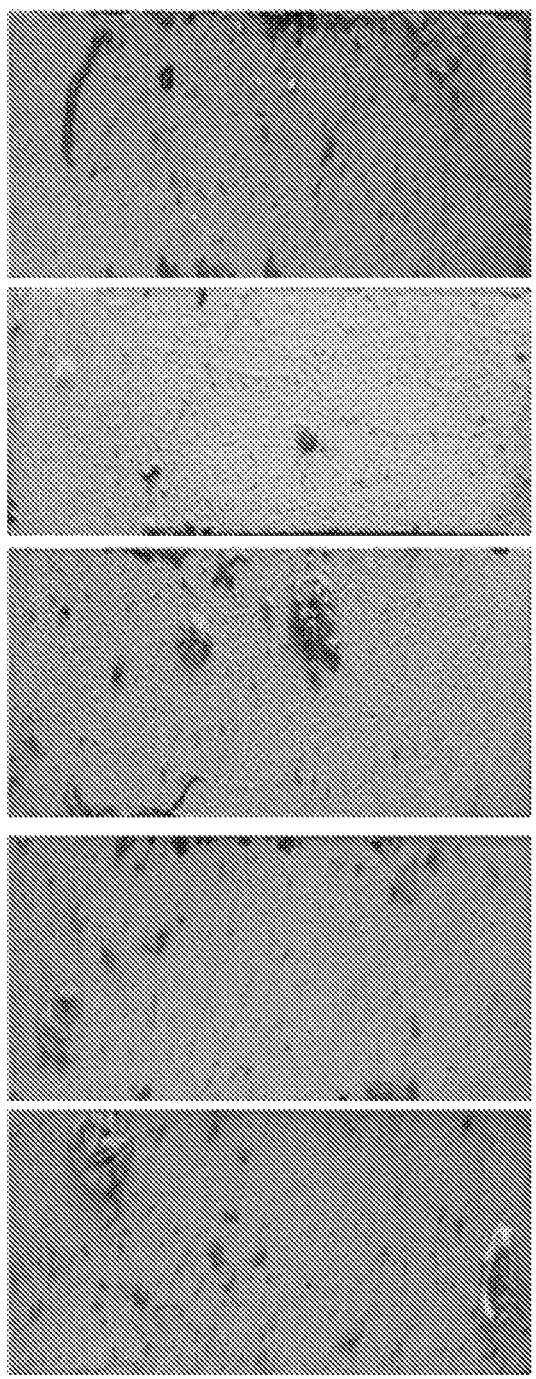
Figure 6:
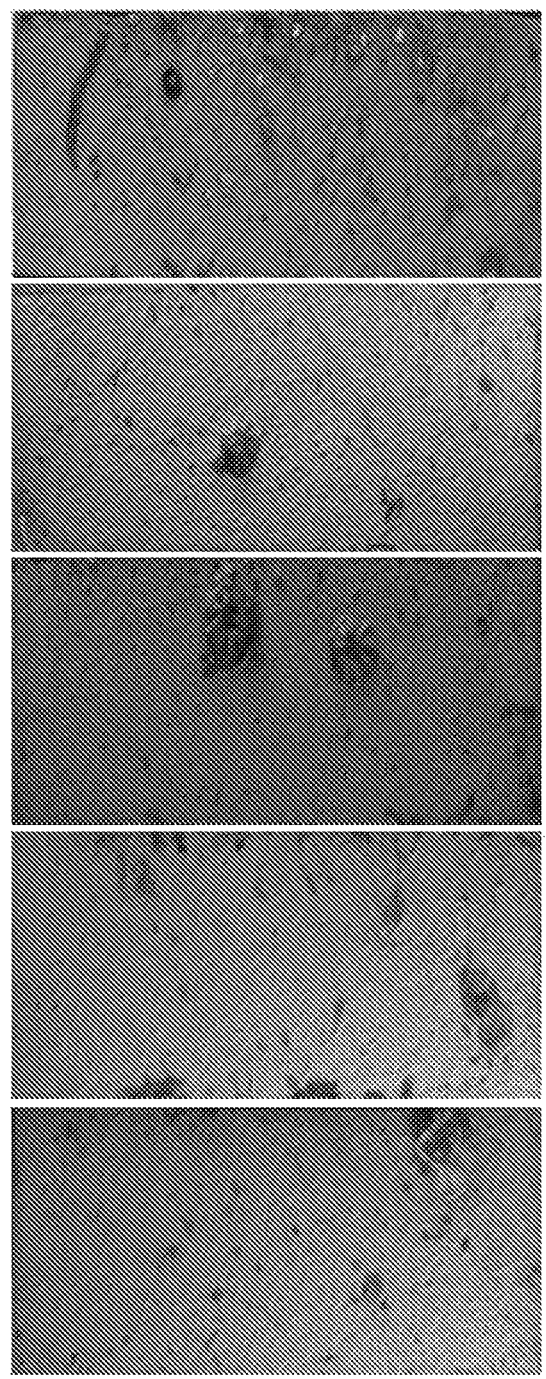
Figure 7:
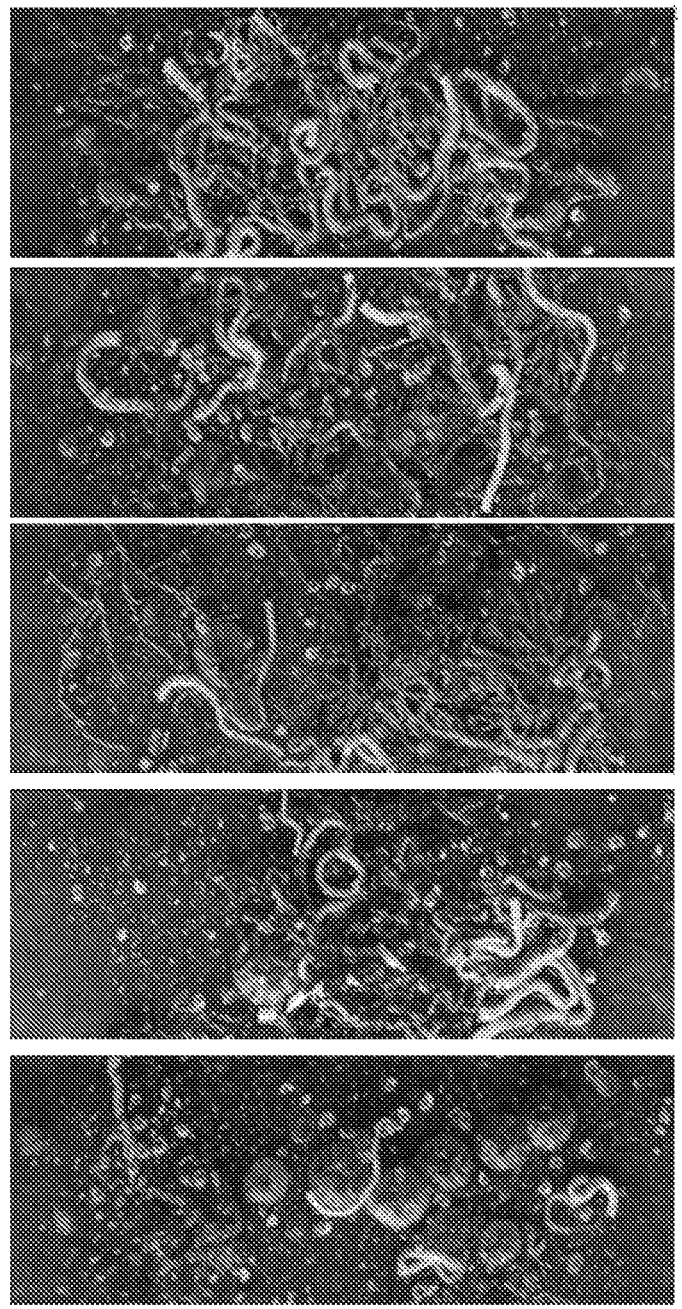
FIG. 7 is a photograph that shows the appearance of coated and uncoated glass slides after 6 weeks of immersion. The glass slides are coated with selected polyurethanes derived from diols bearing two quaternary ammonium salts.
Figure 7:
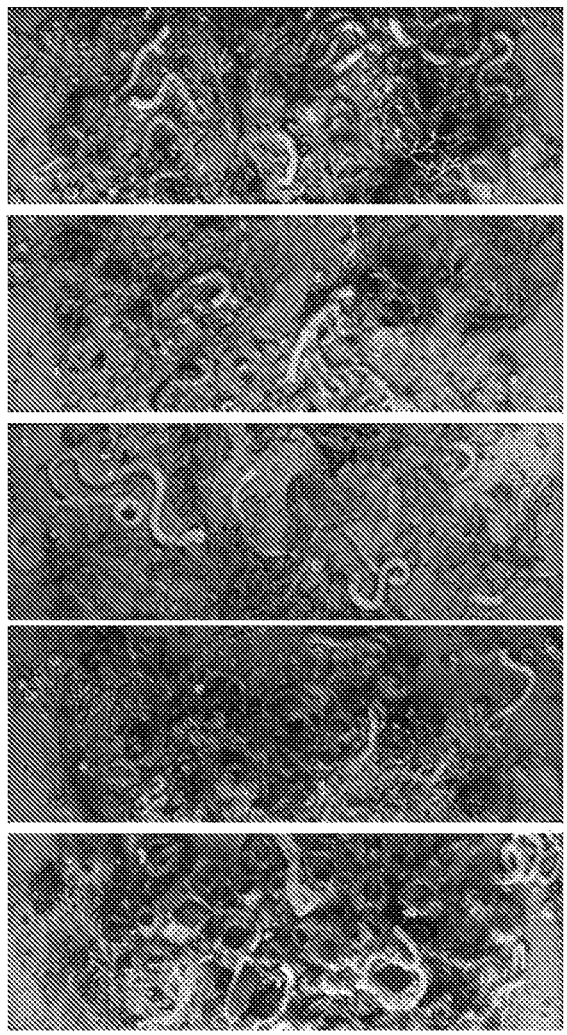
Figure 7:
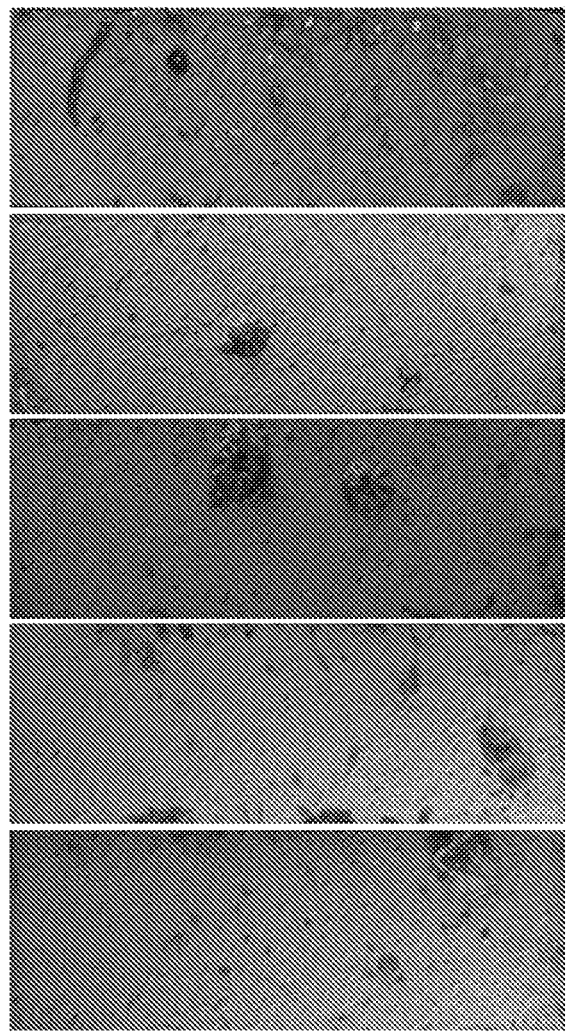
Figure 8:
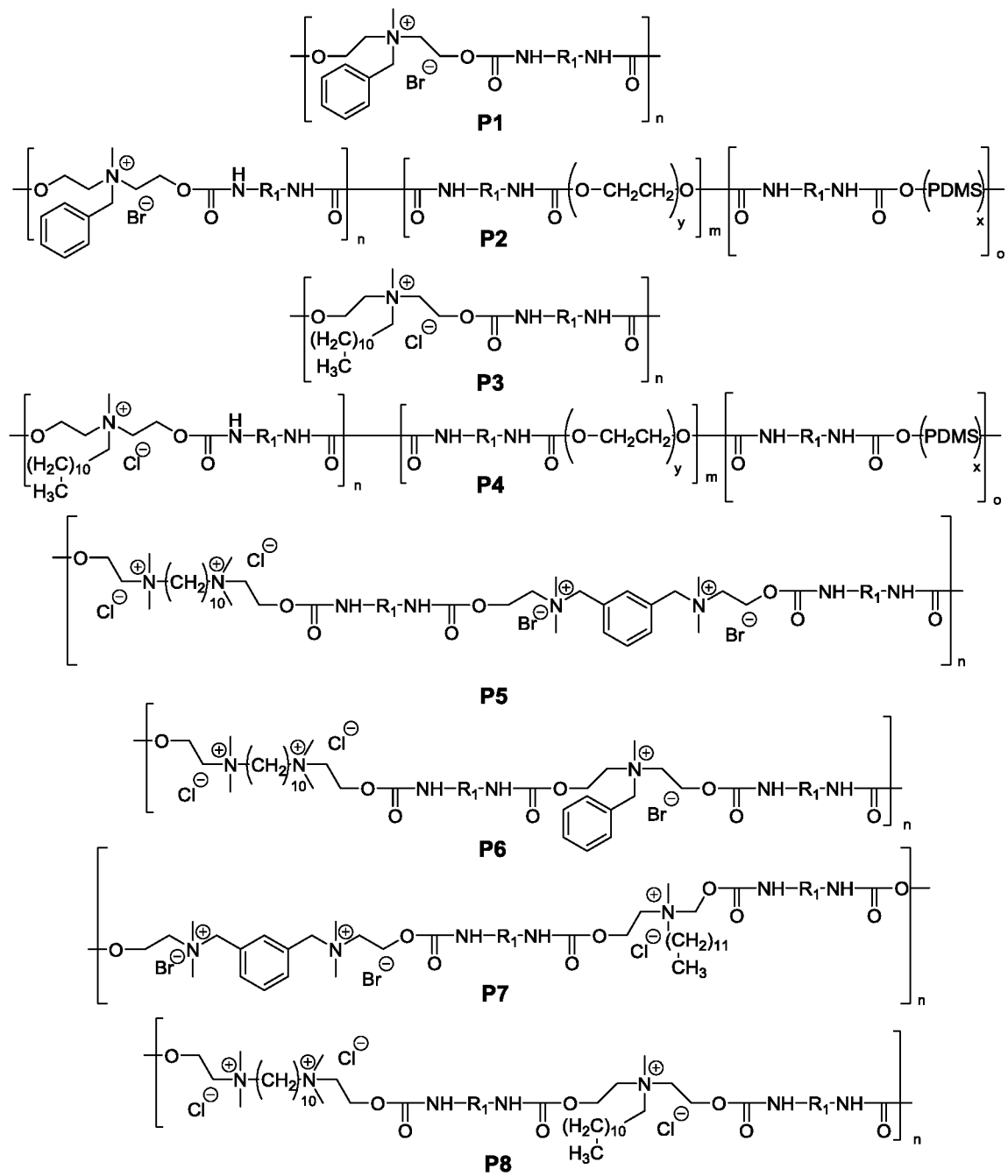
FIG. 8 shows various chemical structures of polyurethanes used in the examples described herein.

Since the antifouling activity of mono quaternary ammonium salt bearing homo and copolyurethanes was somewhat inadequate, diols bearing two quaternary ammonium salt groups were designed and synthesized as shown in Scheme 4. Homo and copolyurethanes were prepared from diols bearing two quaternary ammonium salts (Schemes 5 and 6, respectively). Among the various combinations studied this class of polymers showed superior antifouling properties which is highly desired since the performance is equal or nearly comparable to that of biocide based antifouling solutions. Because of the non-leaching, active by contact nature, antifouling surfaces formed by these polymers are highly preferred. The antifouling behavior of selected polyurethanes derived from diols bearing two quaternary ammonium salts is shown in FIG. 5. As can be noted from the figure, even though the exposure is only for two weeks, the fouling pressure was very high can be noted from the blank glass slide as well as that coated with the primer. Photographs (FIGS. 6 and 7) of the slides coated with selected polyurethanes derived from diols bearing two quaternary ammonium salts also revealed that these were completely free of tube worms. Tubeworms are one of the fouling organisms abundantly present in the waters surrounding Singapore and are also active throughout the year. A closer look at the nature of barnacle settlement at the reference slides clearly indicate that these organisms settled at very early stage of immersion and were abundant. A comparison between the reference slides and that of those coated with selected polyurethanes derived from diols bearing two quaternary ammonium salts clearly point to the superior performance in terms of not only hard fouling but also against soft fouling.

Scheme 4. Preparation of diol monomers bearing two quaternary ammonium salts

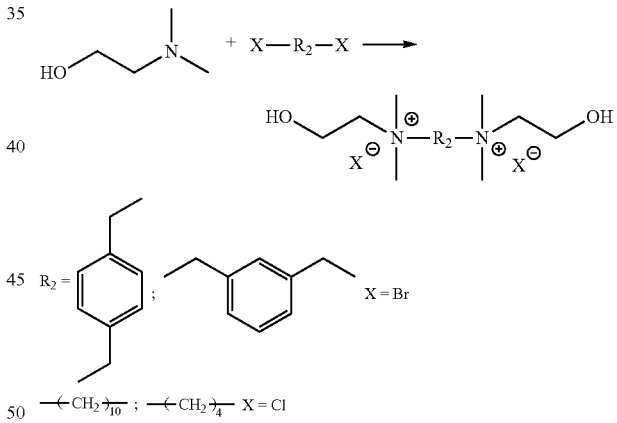

Scheme 5. Preparation of homo polyurethanes from diol monomers bearing two quaternary ammonium salts

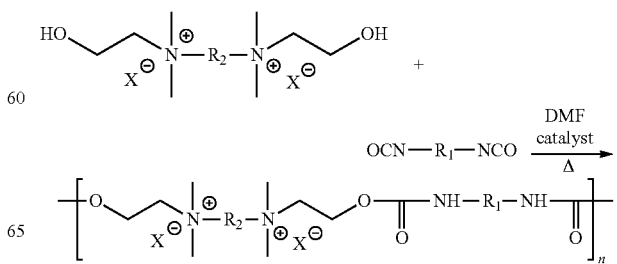

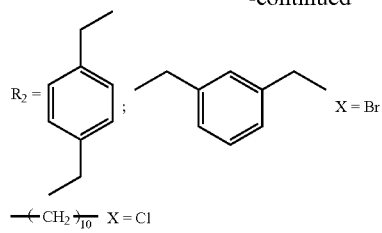

Scheme 6. Preparation of copolyurethanes from diol monomers bearing two quaternary ammonium salts

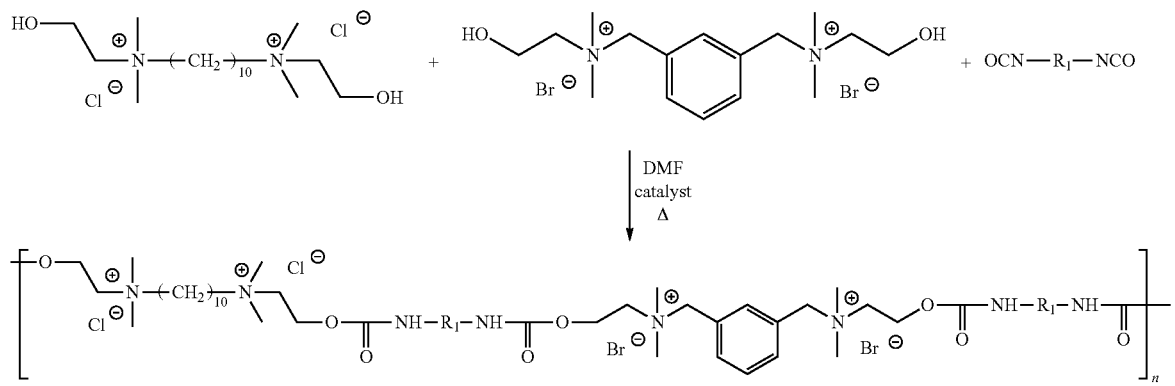

Details on Matrix Assisted Laser Desorption and Ionization (MALDI) Characterization Matrix Assisted Laser Desorption and Ionization Time-of-Flight-Mass Spectroscopy (MALDI-ToF MS) analyses of polymers were carried out using Bruker Autoflex speed system with 2,5-dihydroxybenzoic acid matrix with silver trifluoroacetate cationization agent. The matrix was dissolved in methanol at 10 mg/mL concentration. The sample and cationzation agent prepared at 2.0 mg/mL concentration and mixed 10:1:1 ratios. Each spectra were collected approximately 5000 laser shots on linear mode either positive or negative technique. The molecular weight and molecular weight distribution of copolymer samples were calculated using Polymerix software.

Preparation of Diol Monomers Bearing one Quaternary Ammonium Salt

N,N-Bis(2-hydroxyethyl)-N-methyl dodecyl ammonium bromide (DEA-BDD)

N-methyldiethanolamine (4.9686 g, 0.042 mol) was added to a single neck round bottom flask. The flask was then fitted with a drying tube and stirred using a magnetic stirrer. Bromododecane (10 mL, 0.042 mol) was added slowly through a syringe to control the exothermic mixing. After completing the addition the reaction mixture was stirred under ambient conditions for 30 minutes. It was then immersed in a preheated oil bath maintained at 80° C. The contents of the flask became viscous and the stirring stopped after 4 h. A waxy solid was obtained upon cooling to room temperature. Yield: 14 g. $^1$H-NMR analysis of the product indicated that the —CH$_3$ group attached to the N atom shifted from 2.2 ppm in the starting material to 3.3 ppm upon quaternization. The methylene group attached to the N atom also shifted to 3.8 ppm.

N,N-Bis(2-hydroxyethyl)-N-methyl dodecyl ammonium chloride (DEA-CDD)

N-methyldiethanolamine (5.0096 g, 0.042 mol) was added to a single neck round bottom flask. The flask was then fitted with a drying tube and stirred using a magnetic stirrer. Chlorododecane (10 mL, 0.043 mol) was added slowly through a syringe to control the exothermic mixing. After completing the addition the reaction mixture was stirred under ambient conditions for 30 minutes. It was then immersed in a preheated oil bath maintained at 100° C. After 42 h the two immiscible phases turned into a single phase. A waxy solid was obtained upon cooling to room temperature. Yield: 12 g. $^1$H-NMR analysis indicated that the —CH$_3$ group attached to the N atom shifted from 2.2 ppm in the starting material to 3.3 ppm after quaternization.

N,N-Bis(2-hydroxyethyl)-N-methyl benzyl ammonium bromide (DEA-BzBr)

N-methyldiethanolamine (10.0293 g, 0.084 mol) was added to a single neck round bottom flask. The flask was then fitted with a drying tube and stirred using a magnetic stirrer. Benzyl bromide (10 mL, 0.084 mol) was added very slowly through a syringe to control the exothermic mixing. After completing the addition the reaction mixture was stirred under ambient conditions and it turned highly viscous within few minutes and solidified. The solidified reaction mixture was kept under ambient conditions overnight. The solid was soaked in dry dichloromethane (50 mL). The solid was broken with the help of spatula, transferred to a sample bottle and dried in a vacuum oven. Yield: 23 g. $^1$H-NMR analysis indicated that the —CH$_3$ group attached to the N atom shifted from 2.2 ppm in the starting material to 3.1 ppm upon quaternization.

N,N-Bis(2-hydroxyethyl)-N-methyl benzyl ammonium chloride (DEA-BzCl)

N-methyldiethanolamine (10.4124 g, 0.087 mol) was added to a single neck round bottom flask. The flask was then fitted with a drying tube and stirred using a magnetic stirrer. Benzyl chloride (10 mL, 0.087 mol) was added very slowly through a syringe to control the exothermic mixing. After completing the addition the reaction mixture was stirred under ambient conditions overnight. The contents of the flask solidified during this period. The solid was soaked in dry dichloromethane (50 mL). Then the solid was broken with the help of spatula, transferred to a sample bottle and dried in a vacuum oven. Yield: 20 g. $^1$H-NMR analysis indicated that the —CH$_3$ group attached to the N atom shifted from 2.2 ppm in the starting material to 3.2 ppm after quaternization.

Preparation of Diol Monomers Bearing two Quaternary Ammonium Salts

Reaction product of N,N-dimethylaminoethanol and 1,10-dichlorodecane (AE-DCD)

N,N-dimethylaminoethanol (4.216 g, 0.047 mol) was added to a single neck round bottom flask. The flask was then fitted with a drying tube and stirred using a magnetic stirrer. 1,10-dichlorodecane (5 mL, 0.024 mol) was added slowly through a syringe to control the exothermic mixing. After completing the addition the reaction mixture was stirred under ambient conditions for 30 minutes. It was then immersed in a preheated oil bath maintained at 80° C. The contents of the flask solidified after heating for 4 h. The solid was washed with diethyl ether and dried in a vacuum oven. Yield: 6 g. $^1$H-NMR analysis indicated that the —$CH_3$ group attached to the N atom shifted to 3.3 ppm after quaternization.

Reaction product of N,N-dimethylaminoethanol and 1,4-dichlorobutane (AE-DCB)

N,N-dimethylaminoethanol (16.284 g, 0.2 mol) was added to a single neck round bottom flask. The flask was then fitted with a drying tube and stirred using a magnetic stirrer. 1,4-dichlorobutane (10 mL, 0.1 mol) was added slowly through a syringe to control the exothermic mixing. After completing the addition the reaction mixture was stirred under ambient conditions overnight. $^1$H-NMR analysis of the reaction mixture indicated that no reaction occurred. It was then immersed in a preheated oil bath maintained at 80° C. The contents of the flask solidified within 30 minutes. The flask was cooled and the solid was washed with diethyl ether and dried in a vacuum oven. Yield: 20 g. $^1$H-NMR analysis indicated that the —$CH_3$ group attached to the N atom shifted to 3.1 ppm after quaternization.

Reaction product of N,N-dimethylaminoethanol and α,α'-dibromo-m-xylene (AE-mX)

α,α'-dibromo-m-xylene (7.8887 g, 0.03 mol) was dissolved in dry dichloromethane (40 mL) in single neck round bottom flask. The flask was then fitted with a drying tube. N,N-dimethylaminoethanol (5.316 g, 0.06 mol) was added slowly through a syringe to control the exothermic reaction. The reaction mixture immediately turned milky and a separate liquid layer was formed. The reaction mixture was stirred under ambient conditions for 24 h. Dichloromethane was decanted off. The residue was washed with dichloromethane (2×25 mL) and dried in a rotavapor. Yield: 10 g. $^1$H-NMR analysis indicated that the —$CH_3$ group attached to the N atom shifted to 3.3 ppm upon quaternization.

Reaction product of N,N-dimethylaminoethanol and α,α'-dibromo-p-xylene (AE-pX)

α,α'-dibromo-m-xylene (7.8778 g, 0.03 mol) was dissolved in dry dichloromethane (80 mL) in single neck round bottom flask. The flask was then fitted with a drying tube. N,N-dimethylaminoethanol (5.316 g, 0.06 mol) was added slowly through a syringe to control the exothermic reaction. The reaction mixture immediately turned milky and afterwards a white solid separated from the reaction mixture. The reaction mixture was stirred under ambient conditions for 24 h. Dichloromethane was decanted off. The residue was washed with dichloromethane (2×25 mL) and dried in a rotavapor. Yield: 12 g. The product was insoluble in organic solvents as well as in water.

Preparation of Homopolyurethanes

Preparation of P1

DEA-BzBr (2.3611 g, 0.008 mol) was dissolved in dry N,N-dimethyl formamide (20 mL) in a single neck flask fitted with a drying tube at 80° C. After completely dissolving the solid, dibutyl tin dilaurate (3 drops) was added followed by bis(4-isocyanatocyclohexyl)methane (2 mL, 0.008 mol). The reaction mixture was heated and stirred at 80° C. for 24 h. Then the flask was cooled and the light brown solution was added drop wise into large excess of ethyl acetate (300 mL), stirred well and allowed to settle. The solvent mixture was decanted off, washed again with ethyl acetate (2×25 mL) and dried in a vacuum oven. Yield: 4 g.

Preparation of P3

DEA-CDD (2.682 g, 0.008 mol) was dissolved in dry tetrahydrofuran (25 mL) in a single neck flask fitted with a reflux condenser and a drying tube. After completely dissolving the solid, dibutyl tin dilaurate (3 drops) was added followed by bis(4-isocyanatocyclohexyl)methane (2 mL, 0.008 mol). The reaction mixture was refluxed for 24 h. Then the flask was cooled and the solvent was removed in a rotavapor. The residue was washed with diethyl ether (3×25 mL) and then dried in a vacuum oven. Yield: 4.2 g.

Preparation of AE-DCD-U

AE-DCD (8.2293 g, 0.02 mol) was heated in dry N,N-dimethyl formamide (70 mL) in a single neck flask fitted with a drying tube at 80° C. to form a white dispersion for 15 minutes. Then dibutyl tin dilaurate (0.1634 g, 0.0003 mol) was added followed by bis(4-isocyanatocyclohexyl)methane (5 mL, 0.02 mol). The reaction mixture was heated and stirred at 80° C. for 30 h. Then the flask was cooled and the light brown solution was added drop wise into large excess of ethyl acetate (800 mL), stirred well and allowed to settle. The solvent mixture was decanted off, washed again with ethyl acetate (2×50 mL) and dried in a vacuum oven. Yield: 11 g.

Preparation of AE-mX-U

AE-mX (7.2522 g, 0.02 mol) was heated in dry N,N-dimethyl formamide (60 mL) in a single neck flask fitted with a drying tube at 80° C. to form a clear solution. Then dibutyl tin dilaurate (0.1591 g, 0.0003 mol) was added followed by bis(4-isocyanatocyclohexyl)methane (5 mL, 0.02 mol). The reaction mixture was heated and stirred at 80° C. for 30 h. Then the flask was cooled and the light brown solution was added drop wise into large excess of ethyl acetate (800 mL), stirred well and allowed to settle. The solvent mixture was decanted off, washed again with ethyl acetate (2×50 mL) and dried in a vacuum oven. Yield: 10 g.

Preparation of Copolyurethanes

Preparation of P2

DEA-BzBr (2.0078 g, 0.007 mol), polyethylene glycol (MW 600) (1.715 g, 0.003 mol), and bishydroxy terminated polydimethyl siloxane (MW 5600) (1.976 g, 0.0004 mol) were dissolved in dry N,N-dimethyl formamide (25 mL) in a single neck flask fitted with a drying tube at 80° C. After forming a hazy solution, dibutyl tin dilaurate (3 drops) was added followed by bis(4-isocyanatocyclohexyl)methane (2.5 mL, 0.01 mol). The reaction mixture was heated and stirred at 80° C. for 24 h. Then the flask was cooled and the light brown solution was added drop wise into large excess of ethyl acetate (300 mL), stirred well and allowed to settle. The solvent mixture was decanted off, residue washed again with ethyl acetate (2×25 mL) and dried in a vacuum oven. Yield: 6 g.

Preparation of P4

DEA-CDD (2.0469 g, 0.006 mol), polyethylene glycol (MW 600) (1.5553 g, 0.003 mol), and bishydroxy terminated polydimethyl siloxane (MW 5600) (1.8456 g, 0.0003 mol) were dissolved dry tetrahydrofuran (30 mL). After forming a hazy solution, dibutyl tin dilaurate (3 drops) was added followed by bis(4-isocyanatocyclohexyl)methane (2.2 mL, 0.01 mol). The reaction mixture was refluxed for 24 h. Then the flask was cooled and the solvent was removed in a rotavapor. The residue was washed with diethyl ether (3×25 mL) and then dried in a vacuum oven. Yield: 6.5 g.

Preparation of Polyurethanes from Mixed Monomers

Preparation of P5

AE-DCD (4.1156 g, 0.01 mol) and AE-mX (3.6702 g, 0.01 mol) were heated in dry N,N-dimethyl formamide (60 mL) in a single neck flask fitted with a drying tube at 80° C. for 15 minutes. Then dibutyl tin dilaurate (0.1692 g, 0.0003 mol) was added followed by bis(4-isocyanatocyclohexyl)methane (5.1 mL, 0.02 mol). The reaction mixture was heated and stirred at 80° C. for 30 h. Then the flask was cooled and the light brown solution was added drop wise into large excess of ethyl acetate (800 mL), stirred well and allowed to settle. The solvent mixture was decanted off, washed again with ethyl acetate (2×50 mL) and dried in a vacuum oven. Yield: 11 g. Molecular weight (as determined by MALDI): $M_n$=6060 $M_w$=7860 PD=1.3.

Preparation of P6

AE-DCD (1.2907 g, 0.003 mol) and DEA-BzBr (1.1823 g, 0.004 mol) were heated in dry N,N-dimethyl formamide (20 mL) in a single neck flask fitted with a drying tube at 80° C. until DEA-BzBr dissolved completely. Then dibutyl tin dilaurate (3 drops) was added followed by bis(4-isocyanatocyclohexyl)methane (1.7 mL, 0.007 mol). The reaction mixture was heated and stirred at 80° C. for 30 h. Then the flask was cooled and the light brown solution was added drop wise into large excess of ethyl acetate (300 mL), stirred well and allowed to settle. The solvent mixture was decanted off, washed again with ethyl acetate (2×25 mL) and dried in a vacuum oven. Yield: 3.8 g. Molecular weight (as determined by MALDI): $M_n$=4130 $M_w$=5600 PD=1.4.

Preparation of P7

DEA-CDD (1.0125 g, 0.003 mol) and AE-mX (1.1509 g, 0.003 mol) were heated in dry N,N-dimethyl formamide (20 mL) in a single neck flask fitted with a drying tube at 80° C. to form a clear solution. Then dibutyl tin dilaurate (3 drops) was added followed by bis(4-isocyanatocyclohexyl)methane (1.5 mL, 0.006 mol). The reaction mixture was heated and stirred at 80° C. for 24 h. Then the flask was cooled and the light brown solution was added drop wise into large excess of ethyl acetate (300 mL), stirred well and allowed to settle. The solvent mixture was decanted off, washed again with ethyl acetate (2×25 mL) and dried in a vacuum oven. Yield: 3 g.

Preparation of P8

DEA-CDD (1.1104 g, 0.003 mol) and AE-DCD (1.3064 g, 0.003 mol) were heated in dry N,N-dimethyl formamide (20 mL) in a single neck flask fitted with a drying tube at 80° C. for 15 minutes. Then dibutyl tin dilaurate (4 drops) was added followed by bis(4-isocyanatocyclohexyl)methane (1.6 mL, 0.006 mol). The reaction mixture was heated and stirred at 80° C. for 24 h. Then the flask was cooled and the light brown solution was added drop wise into large excess of ethyl acetate (300 mL), stirred well and allowed to settle. The solvent mixture was decanted off, washed again with ethyl acetate (2×25 mL) and dried in a vacuum oven. Yield: 3.5 g. Molecular weight (as determined by MALDI): $M_n$=5400 $M_w$=7500 PD=1.4.

UV Curing of Polyurethanes

Step 1—Preparation of Polyurethane Diol Macromer

AE-DCD (0.8746 g, 0.0023 mol) and AE-mX (1.0421 g, 0.0024 mol) were heated in dry N,N-dimethyl formamide (10 mL) in a single neck flask fitted with a drying tube at 80° C. for 15 minutes. Then dibutyl tin dilaurate (0.0956 g, 0.0002 mol) was added followed by bis(4-isocyanatocyclohexyl)methane (1 mL, 0.004 mol). The reaction mixture was heated and stirred at 80° C. for 24 h.

Step 2—Reactive Curing Under UV Light

Photoinitiator, 2,2-dimethoxy-1,2-dipheny ethan-1-one (0.01 g, 0.00004 mol) was added to the macromer solution of step 1 at room temperature and stirred well. Methyl methacrylate (0.468 g, 0.005 mol) was then added and stirred. This solution was then transferred to a petri dish. Isocyanatoethyl methacrylate (0.66 g, 0.004 mol) was added throughout the macromer solution in the petri dish and exposed to UV light for 2 h. Then the dish was taken out and the supernatant liquid was collected in a beaker. The petri dish was treated with dichloromethane followed by methanol and allowed to dry under ambient conditions to yield a pale yellow solid, broken film. Yield: 1.83 g (45%). The solution collected from the petri dish yielded 1.4783 g (50%) of solid after precipitation in ethyl acetate followed by drying in vacuum oven.

Preparation of Sol-Gel Coating Using Polyurethanes

Step 1—Preparation of Polyurethane Diol Macromer

AE-DCD (0.9083 g, 0.0023 mol) and AE-mX (1.0368 g, 0.0023 mol) were heated in dry N,N-dimethyl formamide (10 mL) in a single neck flask fitted with a drying tube at 80° C. for 15 minutes. Then dibutyl tin dilaurate (0.092 g, 0.0002 mol) was added followed by bis(4-isocyanatocyclohexyl)methane (1 mL, 0.004 mol). The reaction mixture was heated and stirred at 80° C. for 24 h. Then the reaction solution was cooled down to room temperature. Triethoxysilyl propylisocyanate (0.999 g, 0.004 mol) was added and stirred overnight under ambient conditions.

Step 2—Gelation

The macromer solution of step 1 was transferred to a 100 mL beaker. Hydroxy terminated polydimethyl siloxane (MW 4670) (14.2425 g, 0.003 mol) was added followed by tetrabutylammonium fluoride solution (1 mM solution in tetrahydrofuran) (0.5 mL) and stirred well. The beaker was subsequently immersed in an oil bath and heated at 60° C. for 24 h. The beaker was then cooled, washed with dichloromethane followed by methanol and dried in a vacuum oven. Yield: 6.3117 g.

Coating of Frosted Glass Slides of 7 cm×2 cm

About 1 g of polymer was dissolved in 2 mL of methanol. To this solution 8 mL of Primacon (commercial primer for underwater coatings) was added and stirred well. This mixture was coated on five frosted glass plates with the help of doctor blade and allowed to develop under ambient conditions. After 1 week, the glass slides were subjected to leachate test followed by immersion in sea. Two sets of references were used, one uncoated glass slides and the other coated with Primacon alone. The immersed glass slides were subjected to photogrid analysis after exposure for periods of two weeks or above.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A polymer comprising repeating units of P5, P6, P7 or P8:

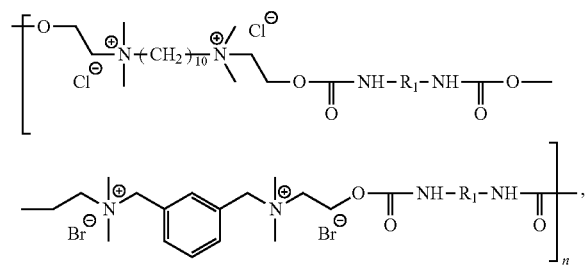

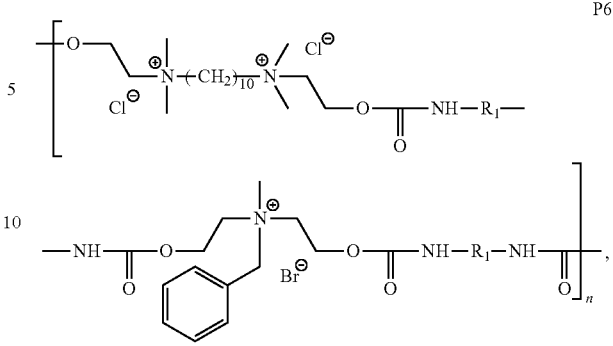

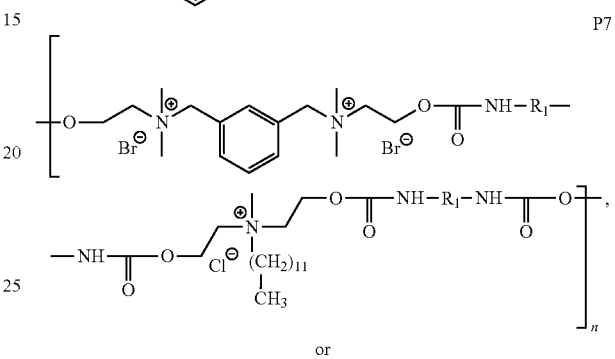

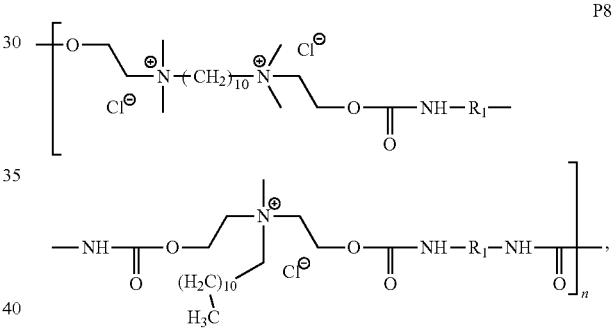

wherein $R_1$ is $C_6$-$C_{20}$ alkylcycloalkyl;
n is any integer from 1 to 100.

2. A method of making a surface antifouling, comprising coating the surface with the polymer of claim 1.

3. The method of claim 2, wherein prior to coating the surface, the polymer is first blended with a primer used in marine coatings.

* * * * *